US00PP21705P2

(12) United States Plant Patent
Benson

(10) Patent No.: US PP21,705 P2
(45) Date of Patent: Feb. 8, 2011

(54) ***AGAPANTHUS* PLANT NAMED 'BENFRAN'**

(50) Latin Name: ***Agapanthus praecox* ssp. *orientalis***
Varietal Denomination: Benfran

(76) Inventor: Frank Benson, 172 Wadeville Street, Pallara, Brisbane, Queensland (AU) H110

( * ) Notice: Subject to any disclaimer, the term of this patent is extended or adjusted under 35 U.S.C. 154(b) by 0 days.

(21) Appl. No.: 12/319,515

(22) Filed: Jan. 8, 2009

(51) Int. Cl.
*A01H 5/00* (2006.01)

(52) U.S. Cl. ..... Plt./398
(58) Field of Classification Search ..... Plt./398
See application file for complete search history.

(56) References Cited

PUBLICATIONS

Avondale Nurseries Ltd. Forward Order Catalogue 2007 [retrieved on Feb. 16, 2010] on the Internet at <http://www.avondalenurseries.org.au/ANstores/_images/2007%20Forward%20Order%20Catalogue.pdf> 10pp.*

* cited by examiner

*Primary Examiner*—June Hwu

(57) ABSTRACT

A new and distinct *Agapanthus* cultivar named 'Benfran' is disclosed, characterized by a very short plant form, strong clump formation and an average of at least 5 flowering stems during the flowering season. The new variety is an *Agapanthus*, normally produced as an outdoor garden or container plant.

1 Drawing Sheet

Figure 1:
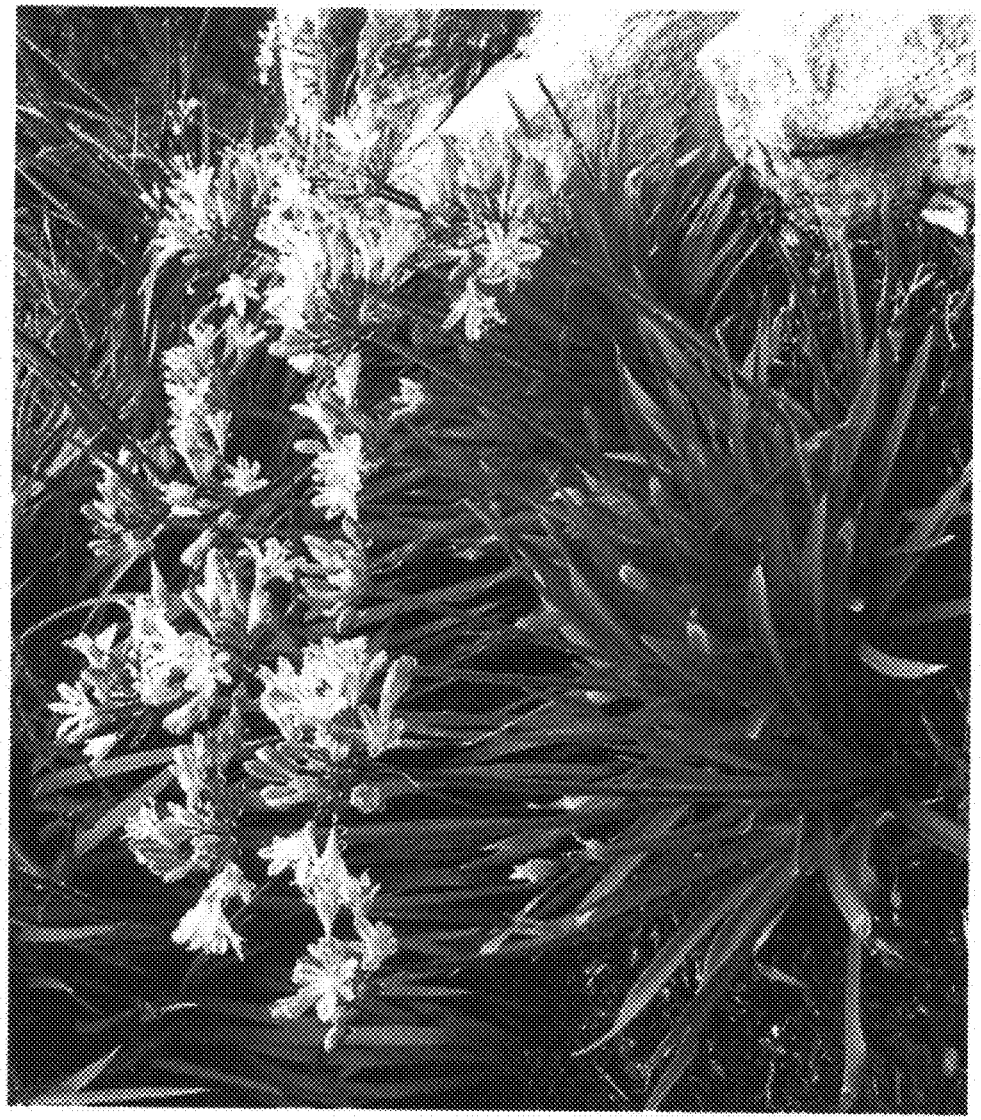

Latin name of the genus and species: *Agapanthus praecox* ssp. *orientalis*.

Variety denomination: 'Benfran'.

BACKGROUND OF THE INVENTION

The new cultivar was discovered as a spontaneous, whole plant mutation of the unpatented variety *Agapanthus praecox* ssp. *orientalis* 'Peter Pan' by the inventor, Frank Benson. The new variety was found in a commercial planting of 'Peter Pan' in a nursery in Pallara, Australia. Originally 3 shorter plants were observed in the commercial planting of 'Peter Pan.' In 2004 a single plant was selected, which is the new cultivar 'Benfran.'

Asexual reproduction of the new cultivar 'Benfran' by tissue culture was first performed in a commercial laboratory in Dodges Ferry, Tasmania Australia, during 2004, and has shown that the unique features of this cultivar are stable and reproduced true to type on successive generations.

SUMMARY OF THE INVENTION

The cultivar 'Benfran' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Benfran' These characteristics in combination distinguish 'Benfran' as a new and distinct *Agapanthus* cultivar:

1. Distinctive flower light violet to white flower coloration
2. Very compact plant size.
3. Strong clump formation.
4. Production of an average of at least 5 flowering scapes continuously during flowering season.

PARENT COMPARISON

Plants of the new cultivar 'Benfran' are similar to plants of the parent variety, *Agapanthus praecox* ssp. *orientalis* 'Peter Pan' in most horticultural characteristics, however, plants of the new cultivar 'Benfran' are shorter and produce more flowering stems than the parent variety.

COMMERCIAL COMPARISON

Plants of the new *Agapanthus* are best compared to the parent variety, as it is the most similar commercial *Agapanthus* to 'Benfran.'

BRIEF DESCRIPTION OF THE PHOTOGRAPH

The accompanying photograph in FIG. 1 illustrates in full color typical plants of 'Benfran' and 'Peter Pan' grown outdoors in New South Wales, Australia, during Spring and Summer, in approximately 15 cm nursery pots. Age of the plants photographed are approximately 2 years from a tissue culture planetlet.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Benfran' plants grown outdoors in New South Wales, Australia The growing temperature ranged from 20° C. to 26° C. during the day and approximately 14° C. to 19° C. at night. The plants were not grown with any kind of shade protection and subject to outdoor, high light conditions. Measurements and numerical values represent averages of typical plant types. No growth retardants were used.

Botanical classification: *Agapanthus praecox* ssp. *orientalis* 'Benfran.'

PROPAGATION

Time to initiate roots: About 30 days at approximately 20° C.

Root description: Typical *Agapanthus* root, freely branching and white-brown in color.

Propagation method: Vegetative divisions or tissue culture.

PLANT

Growth habit: Clump forming.

Age of plant described: Approximately 2 years.

Container size: Approximately 20 cm.

Height: Approximately 27 cm to top of highest leaf. Approximately 38 cm to top of highest inflorescence.

Plant spread: Approximately 22 cm.

Growth rate: Slow.

Branching characteristics: Non-branching, forms basal clumps.

FOLIAGE

Leaf:

*Arrangement.*—Basal, irregular whorls.

*Average length.*—Approximately 30 cm.

*Average width.*—Approximately 1.9 cm.

*Shape of blade.*—Linear.

*Apex.*—Acute.

*Base.*—Cuneate.

*Margin.*—Entire.

*Texture of top surface.*—Smooth.

*Texture of bottom surface.*—Smooth.

*Quantity of leaves per plant.*—Approximately 60.

*Color.*—Young foliage upper side: Near RHS Yellow-Green 146B. Young foliage under side: Near RHS Yellow-Green 146B. Mature foliage upper side: Near RHS Yellow-Green 146A. Mature foliage under side: Near RHS Yellow-Green 146A.

*Venation.*—Type: Linear. Venation color upper side: Near RHS Green 138A. Venation color under side: Near RHS Green 138A.

FLOWER

Natural flowering season: Naturally flower summer through late Autumn.

Inflorescence type and habit: Scapose with single campanulate flower; flowers arranged in umbels on erect scapes.

Rate of flower opening: Approximately 1 week from bud to fully opened flower.

Flower longevity on plant: At least 25 days, after fully opened. Self cleaning.

Quantity of flowers: Plants have approximately 8 open flowers per inflorescence at all times and approximately 12 buds. Average 5 flowering scapes per plant.

Umbel inflorescence size:

*Height.*—Approximately 8 cm.

*Width.*—Approximately 12 cm.

Corolla:

*Arrangement.*—Apetalous, single, campanulate flowers composed of 6 basally fused tepals, shaped into a flared trumpet.

*Size.*—Length: Approximately 3.1 cm. Width: Approximately 2.6 cm at widest point. Lobe length: Approximately 2.1 cm. Lobe width: 0.4 cm.

*Margin.*—Entire.

*Shape.*—Lanceolate, strongly concave while maturing, opening to become reflexed back.

*Apex.*—Obtuse, concave.

*Texture.*—Glabrous.

Color:

*Tepals.*—When opening: Outer surface: Near RHS Violet-Blue 92B with Violet-Blue 92D and White N155A. Inner surface: Near RHS Violet-Blue 92B with Violet-Blue 92D and White N155A.

*Fully opened.*—Outer surface: Near RHS Violet-Blue 92B with Violet-Blue 92D and White N155A. Inner surface: Near RHS Strong mid vein of Violet-Blue 92B with Violet-Blue 92D and White N155A. Color changes when aging: No color change.

*Bud.*—Shape: Ovate to Lanceolate. Length: Approximately 2.7 cm. Diameter: Approximately 0.7 cm. Color: Near RHS Violet-Blue 92B.

Sepals: Not Present.

Pedicels:

*Length.*—Approximately 4.8 cm.

*Width.*—Approximately 0.1 cm.

*Aspect.*—Straight.

*Color.*—Near RHS Green 143B.

*Texture.*—Smooth.

Scape:

*Length.*—Approximately 30 cm.

*Width.*—Approximately 0.8 cm.

*Angle.*—Upright from center of plant, very straight.

*Strength.*—Strong.

*Color.*—Near RHS Green 143A.

*Texture.*—Smooth.

Fragrance: None.

REPRODUCTIVE ORGANS

Stamens:

*Number.*—Average 6.

*Filament length.*—Approximately 3 cm.

*Filament color.*—Near RHS 92D.

*Anther length.*—0.2 cm.

*Anther color.*—Tip Near RHS Yellow-Orange 15D, lower near RHS Greyed-Purple 186A.

*Anther shape.*—Oblong.

*Pollen.*—Scant.

*Pollen color.*—Near RHS Yellow 7A.

Pistil:

*Number.*—1.

*Length.*—Approximately 2.8 cm.

*Style color.*—Near RHS Violet-Blue 92D.

*Stigma.*—Shape: Linear. Color: Near RHS Violet-Blue 92A.

*Ovary color.*—Near RHS Yellow-Green 150B.

OTHER CHARACTERISTICS

Seeds and fruits: Not observed to date.

Disease/pest resistance: Neither resistance nor susceptibility to pathogens and pests common to *Agapanthus* have been observed.

Temperature tolerance: Tolerates temperatures from approximately 0-1 C to 40°C.

What is claimed is:

1. A new and distinct cultivar of *Agapanthus* plant named 'Benfran' as herein illustrated and described.

* * * * *